(12) United States Patent
Fuhr et al.

(10) Patent No.: US 7,070,684 B1
(45) Date of Patent: Jul. 4, 2006

(54) ELECTRODE ARRANGEMENT FOR GENERATING FUNCTIONAL FIELD BARRIERS IN MICROSYSTEMS

(75) Inventors: Günter Fuhr, Berlin (DE); Thomas Schnelle, Berlin (DE); Rolf Hagedorn, Berlin (DE); Torsten Müller, Berlin (DE)

(73) Assignee: Evotec Technologies GmbH, Duesseldorf (DE)

( * ) Notice: Subject to any disclaimer, the term of this patent is extended or adjusted under 35 U.S.C. 154(b) by 0 days.

(21) Appl. No.: 09/720,275

(22) PCT Filed: Jun. 28, 1999

(86) PCT No.: PCT/EP99/04470

§ 371 (c)(1),
(2), (4) Date: Feb. 22, 2001

(87) PCT Pub. No.: WO00/00293

PCT Pub. Date: Jan. 6, 2000

(30) Foreign Application Priority Data

| Jun. 26, 1998 | (DE) | ................................. 198 28 626 |
| Jun. 29, 1998 | (DE) | ................................. 198 28 919 |
| Nov. 20, 1998 | (DE) | ................................. 198 53 658 |
| Dec. 23, 1998 | (DE) | ................................. 198 60 118 |

(51) Int. Cl.
*G01N 27/447* (2006.01)
*G01N 27/453* (2006.01)

(52) U.S. Cl. ........................................ 204/547; 204/643

(58) Field of Classification Search ................ 204/450, 204/547, 600, 643; 209/127.1, 128, 129, 209/130, 131, 132, 155

See application file for complete search history.

(56) References Cited

U.S. PATENT DOCUMENTS

| 3,197,394 A | | 7/1965 | McEuen ..................... 204/186 |
| 3,674,198 A | | 7/1972 | Eberle ......................... 233/26 |
| 4,326,934 A | * | 4/1982 | Pohl ........................... 204/547 |
| 4,726,904 A | | 2/1988 | Ayers ......................... 210/658 |
| 4,764,473 A | | 8/1988 | Matschke et al. ........... 435/287 |
| 4,804,355 A | | 2/1989 | Brimhall et al. ............. 494/20 |

(Continued)

FOREIGN PATENT DOCUMENTS

DE          1966274         7/1972

(Continued)

OTHER PUBLICATIONS

Wang et al., "Dielectrophoretic Manipulation of Particles," Conference Record of the 1995 IEEE 30th IAS Annual Meeting, vol. pp. 1358-1365 (1995).*

(Continued)

*Primary Examiner*—Alex Noguerola
(74) *Attorney, Agent, or Firm*—Baker Botts LLP (57) ABSTRACT

A microsystem adapted for dielectrophoretic manipulation of particles in a suspension liquid wherein the microsystem has a channel with channel walls and a longitudinal extension. An electrode arrangement is present which has at least one microelectrode on at least one of the channel walls. This acts to generate a field barrier which crosses the channel at least partly. The microelectrode has a band-shape or has a multitude of straight electrode sections connected to each other. The band-shape has a predetermined curvature or the straight electrode sections are arranged with predetermined different angles so that the field barrier has a predetermined curvature relative to the longitudinal extension of the channel.

10 Claims, 10 Drawing Sheets

U.S. PATENT DOCUMENTS

| | | | |
|---|---|---|---|
| 4,941,969 A | | 7/1990 | Schonert et al. .............. 209/39 |
| 5,489,506 A | * | 2/1996 | Crane ............................ 435/2 |
| 5,565,105 A | | 10/1996 | Thakor ....................... 210/695 |
| 5,593,565 A | | 1/1997 | Ajdari et al. ............... 204/643 |
| 5,814,200 A | * | 9/1998 | Pethig et al. ............... 204/547 |
| 5,858,192 A | * | 1/1999 | Becker et al. .............. 204/547 |
| 5,888,370 A | * | 3/1999 | Becker et al. .............. 204/643 |
| 2002/0175079 A1 | * | 11/2002 | Christel et al. ............. 204/601 |

FOREIGN PATENT DOCUMENTS

| | | |
|---|---|---|
| DE | 3317415 | 11/1984 |
| DE | 3610303 | 2/1987 |
| DE | 8813314 | 2/1989 |
| DE | 19500660 | 6/1996 |
| WO | 9810869 | 3/1998 |

OTHER PUBLICATIONS

Merriam-Webster OnLine definition of hyperbola, downloaded on Mar. 2, 2005 from www.m-w.com/cgi-bin/dictionary?book=Dictionary&va=hyperbola.*

Merriam-Webster OnLine definition of parabola, downloaded on Mar. 2, 2005 from www.m-w.com/cgi-bin/dictionary?book=Dictionary&va=parabola.*

"Dielectrophoretic Sorting of Particles and Cells in a Microsystem" by Fiedler et al. (Analytical Chemsitry, vol. 70, No. 9, May 1, 1998, pp. 1909-1915) (XP-00755524).

"Radio-Frequency Microtools for Particle and Live Cell Manipulation" by Muller et al.; (Natur WissenschaftenAufsatze 81, p. 528-535 (1994), month unknown.

"The LabCD™: A Centrifuge-Based Microfluidic Platform for Diagnostics" by Madou et al. (SPIE vol. 3259, 0277-786X/98, pp. 80-93), month unknown.

G. Fuhr et al, "Radio-Frequency Microtools for Particle and Live Cell Manipulation", Naturwissenschaften, 1994, vol. 81, pp. 528-535, month unknown.

M.J. Madou et al., The LabCD™: A Centrifuge-Based Microfluidic Platform for Diagnostics, SPIE, 1998, vol. 3259, pp. 80-93 month unknown.

* cited by examiner

ELECTRODE ARRANGEMENT FOR GENERATING FUNCTIONAL FIELD BARRIERS IN MICROSYSTEMS

This application is a 371 of PCT/EP99/04470, filed Jun. 28, 1999.

The invention relates to electrode arrangements for generating functional field barriers in microsystems adapted for manipulation of suspended particles, in particular functional microelectrodes for dielectrophoretic deflection of microscopic particles, and microsystems equipped with such electrode arrangements as well as their applications.

BACKGROUND OF THE INVENTION

Manipulation of suspended particles in fluidic microsystems is generally known and has for example been described by G. Fuhr et al in "Naturwissenschaften", vol. 81, 1994, p. 528 ff. The microsystems form in particular channel structures through which a suspension fluid flows with the particles to be manipulated. As a rule the cross-sectional area of these channel structures is rectangular, with the width of the channel walls, which in operating position form the top and bottom (bottom/cover surfaces), being greater than the lateral channel walls (lateral surfaces). In the channel structures, microelectrodes are affixed to the channel walls, with high-frequency electrical fields being applied to said microelectrodes. Under the influence of the high-frequency electrical fields, based on negative or positive dielectrophoresis, polarisation forces are generated in the suspended particles, said polarisation forces making possible repulsion from the electrodes and, acting in combination with flow forces in the suspension liquid, making possible manipulation of the particles in the channel. As a rule, the microelectrodes of conventional microsystems are applied as straight electrode bands to the wider channel walls.

To generate the high-frequency electrical fields effective for dielectrophoresis, in each instance two electrode bands act in combination, said electrode bands being located at opposite channel walls, both with the same shape and alignment. For example the straight electrode bands are aligned parallel to the alignment of the channel i.e. the direction of flow of the suspension liquid in the respective channel section or at a predetermined angle transversely to the alignment of the channel. For an effective and safe formation of polaris at ion forces at the particles, the length of the electrode bands exceeds the characteristic dimensions of the particles to be manipulated many times over (by a factor of approx. 20 to 50).

Conventional microsystems have disadvantages in relation to the effectiveness of generating polarisation forces; the stability and longevity of the microelectrodes; and a limited ability of generating force gradients within the channel structure. These disadvantages are in particular linked to the electrode bands which are formed along comparatively long lengths in the channel. The longer an electrode band, the longer a particle flowing past is in the sphere of influence of the electrode band. Consequently, the effectiveness of the respective microelectrode or the field barrier generated by said microelectrode, increases. However, long electrode bands are also more susceptible to malfunction. Faults in workmanship or mechanical loads can cause interruptions which lead to electrode failure. Furthermore, to achieve a force effect which remains constant along the length of the channel, and thus a reproducible force effect, microelectrodes have so far been limited to the above-mentioned straight electrode shape.

Due to the disadvantages mentioned, the application of said fluidic microsystems with dielectrophoretic particle manipulation has been limited to guiding the particles in the channel structure or to deflecting particles from a given flow.

SUMMARY OF THE INVENTION

It is the object of the invention to provide improved micro systems for dielectrophoretic particle deflection, with said arrangements being suitable to overcome the disadvantages of conventional microsystems, and in particular providing enlarged applications and making it possible to generate field barriers which are also effective in covering shorter channel sections. Furthermore it is the object of the invention to provide novel applications for such microsystems.

A microsystem according to the invention is in particular adapted to create field barriers in the microsystem along predetermined reference surfaces, said field barriers extending at least partly across the width of a channel in the microsystem, and comprising predetermined curvatures relative to the longitudinal extension of the channel, to the direction of flow of the suspension liquid in the channel or to the direction of movement of the (non-deflected) particles. In this context the term "reference surface" not only describes a two-dimensional formation but also a spatial region to which the field effect of the respective microelectrodes extends and in which the field barrier for dielectric influencing of the microscopic particles in the microsystem is formed. This spatial region essentially corresponds to a region through which the field lines of the effective microelectrodes pass; in the case of microelectrode pairs acting in combination, said spatial region essentially passes as a curved hypersurface between the microelectrodes, while in the case of individually acting microelectrodes it acts as a hypersurface encompassing the field line distribution of the individually acting microelectrode. Reference surfaces define the locations where polarisation forces in the microscopic particles can effectively be generated. The microelectrodes are designed such that the reference surfaces, depending on the desired function of the respective micro electrodes, have a predetermined curvature in relation to the direction of movement of the particles in the microsystem, so that an optimal combined effect of the polarisation forces and of the mechanical forces is achieved. Therefore the field barriers are also referred to as functional field barriers. The term "curvature" used here does not refer to the curvature of field lines on straight microelectrodes as a result of the field lines exiting into the adjacent space. But rather, "curvature" refers to the shape of the field barriers formed on microelectrodes.

Preferably, the field barriers with the reference surfaces curved according to the invention are formed according to one of the following three basic forms. According to a first variant, an electrode arrangement according to the invention comprises at least one band-shaped, curved microelectrode extending on the wider channel wall (bottom surface and/or cover surface), at least partly across the channel width. In a second variant, at least one microelectrode is provided which is affixed to the narrower channel wall (lateral surface). In the third variant, at least one microelectrode is affixed to the bottom surface and/or the cover surface of the channel and at least one auxiliary electrode is affixed at a distance from the bottom surface or lateral surface of the channel. The auxiliary electrode supplies a deformation of the field lines emanating from the microelectrode or from the microelectrodes at the bottom surfaces or the side surfaces of the channel so that the reference surfaces curved according to the invention, are formed. In all the variants, the respective electrodes (microelectrodes, auxiliary electrodes) per se can be band-shaped or point-shaped or area-shaped. The electrode arrangements of the second and third variant are also referred to as three-dimensional electrode arrangements, because microelectrodes are used which protrude from the planes of the bottom surfaces or lateral surfaces of the channel or which are arranged at a distance from said surfaces.

It is thus a subject of the invention, to optimise microelectrodes in relation to their effect on suspended particles which may comprise natural or synthetic particles, e.g. for generating maximum forces while at the same time causing minimum electrical losses.

The invention provides the following advantages. The design of the microelectrodes can e.g. be adapted to the flow profile in the suspension liquid. This provides the advantage that the microelectrodes can be shorter and can be designed for generating lesser barriers while being equally as effective as conventional microelectrodes in the shape of straight bands. This has an advantageous effect on the lifetime and function of the microelectrodes and thus of the entire microsystems. Moreover the space available in a microsystem can be used more effectively. Furthermore, electrode arrangements are provided with which gradients can be generated, and thus depending on the respective channel region, forces of various strength can be generated. It is for example provided for the field barriers of the microelectrodes to be designed such that larger polarisation forces act upon the particles in the middle of the channel when compared to the particles at the edge of the channel.

The creation of field barriers according to the invention along curved reference surfaces also makes it possible to create novel applications of microsystems, in particular for guiding suspended particles into particular channel regions, for sorting suspended particles according to their passive electrical properties or for collecting or retaining suspended particles in particular channel sections. For this latter application, the microelectrodes are designed so as to comprise a geometric shape for retaining particles in a solution flow or for generating a particle formation. All the applications mentioned provide contactless manipulation of the suspended particles vis-a-vis the microsystem, a feature which is significant in particular for manipulating biological cells or cell components.

Preferred applications are in the field of microsystem technology for separation, manipulation, loading, fusion, permeation, pair formation and aggregate formation of microscopic small particles.

According to a particular embodiment of the invention, particle movement takes place in a microsystem with conventional electrode shapes or electrode shapes according to the invention, under the influence of centrifugal forces and/or gravitational forces.

BRIEF DESCRIPTION OF THE DRAWINGS

Further details and advantages of the invention are provided in the drawings which are described below. The following are shown.

DETAILED DESCRIPTION OF THE INVENTION

Figure 1A:
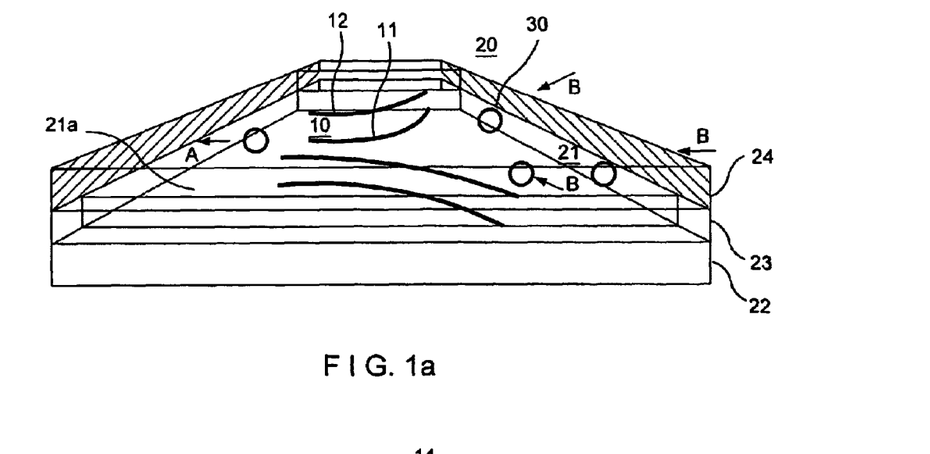
FIGS. 1a to 1d illustrates a diagrammatic perspective views of a channel structure with microelectrodes for generating field barriers in a microchannel and examples of reference surfaces curved according to the invention.

FIG. 1a diagrammatically shows an example of an embodiment of microelectrodes for generating field barriers in microchannels. The fluidic microsystem 20 is shown in sections in distorted perspective lateral view of a channel structure. The channel 21 is formed by two spacers 23 arranged at a distance on a substrate 22, spacers 23 supporting a cover part 24. The width and height of the channel is approx. 200 pm and 40 pm respectively but they can also be less. Such structures are for example made using process techniques of semiconductor technology which are known per see The substrate 22 forms the bottom surface 21a of the channel 21. Accordingly the cover surface (for reasons of clarity not specially emphasised) is formed by the cover part 24. The electrode arrangement 10 comprises microelectrodes 11, 12 attached to the bottom surface 21a or the cover surface. Each of the microelectrodes 11, 12 comprises curved electrode bands which are described in more detail below.

In FIG. 1a the electrode bands form an electrode structure which is explained in detail below, with reference to FIG. 2. The other embodiments, described below, of electrode arrangement according to the invention, can be affixed to the bottom, cover and/or lateral surfaces of the channel 21. A suspension liquid flows through the microchannel 21 (from left to right in the illustration), with particles 30 being suspended in said suspension liquid. For example, it is the task of the electrode arrangement 10 shown in FIG. 1a, to lead the particles 30 from various tracks of movement within the channel to a middle track of movement according to arrow A. To this effect electrical potential is applied to the microelectrodes 11, 12 such that electrical field barriers are generated in the channel which force the particles flowing from the right, to move to the middle of the channel (direction of arrows B).

Typical dimensions of the microelectrodes 11, 12 are 0.1 to some tens of micrometers (typically 5 ... 10 pm) in width, 100 nm to a few micrometers (typically 200 nm) in thickness, and up to several hundred micrometers in length. Due to the small thickness of the electrodes, the interior of the channel 21 is not restricted by the top and bottom of the parts 23, 24 of the electrodes processed. Part 23 is a spacer whose structure forms the lateral channel walls.

The microelectrodes 11, 12 are selected by means of high-frequency electrical signals (typically at a frequency in the MHz range and at an amplitude in the volt range). The respective opposite electrodes 11a, 11b form a control pair although also the electrodes aligned in one plane can combine the effect of their selection action (phase, frequency, amplitude). The electrical high-frequency field generated through the channel 21, i.e. perpendicular to the direction of flow, acts in a polarising way on the suspended particles 30 (which can also be living cells or viruses). At the frequencies mentioned and with suitable conductivity of the suspension liquid surrounding the particles, the particles are repulsed by the electrodes. In this way the hydrodynamically open channel 21 can be structured via the electrical fields with a switch-on and switch-off action, or compartmentalised, or the tracks of movement of the particles in the passive flow field can be influenced. Furthermore, it is possible, despite the permanent flow, to slow down the particles or to position them on station without touching a surface. The type and implementation of the electrode arrangement formed for this purpose also forms part of the invention.

Below, different forms of electrode arrangements according to the invention are described. For reasons of clarity, FIGS. 2 to 13 may only show a planar electrode arrangement (or parts thereof), e.g. on the bottom surface of the channel.

Figure 1B:
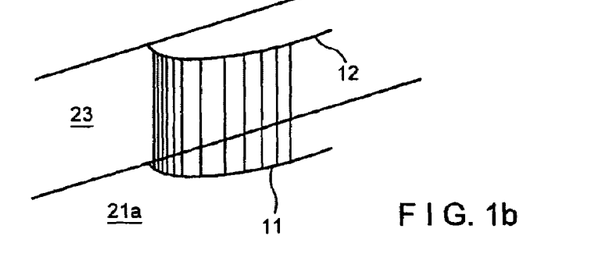
Figure 1C:
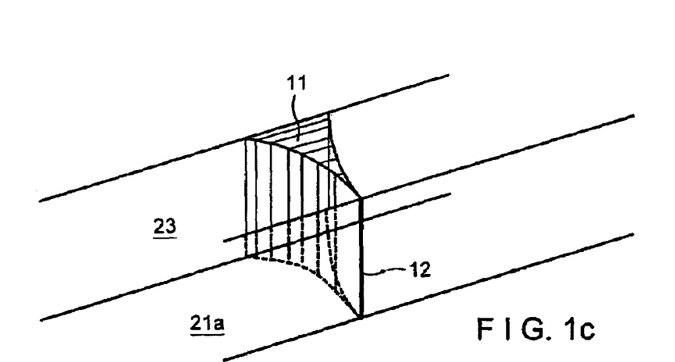

FIGS. 1b to 1c show the basic forms of field barriers or electromagnetic limitations which are implemented with electrode arrangements according to the invention corresponding to the above-mentioned variants. The illustrations are schematic diagrams of the reference surfaces on which the field barriers are formed with microelectrodes according to the invention. For the sake of clarity, only parts of the lateral surface (spacers 23) and of the bottom surface 21a of the channel, the microelectrodes 11, 12 and the shape of the reference surfaces (hatched), are shown.

According to the above-mentioned first variant, the field barrier in the channel is formed between two curved microelectrodes 11, 12 on the bottom or cover surfaces of the channel (FIG. 1b). Accordingly, the reference surface of the field barrier (shown hatched) is a curved surface positioned vertically against the bottom and cover surfaces. If the microelectrodes 11, 12 are for example curved according to a particular hyperbolic flow profile (see below), then the reference surface forms the cutout of the generated surface of a hyperbolic cylinder. If the microelectrodes 11, 12 are not arranged exactly on top of each other, then the reference surface is also oblique-angled in relation to the bottom and cover surfaces of the channel.

According to FIG. 1c, the reference surface, shown hatched, shows a spatial region impinged on by field lines extending from one microelectrode 11 at a lateral surface of the channel to a microelectrode 12 at the opposite lateral surface. In the example shown, the surface of the first microelectrode 11 is larger than that of the second microelectrode 12 so that there is a field line concentration at microelectrode 12. Consequently, the polarisation forces acting from the field barrier on suspended particles are larger near the second microelectrode 12 than near the first microelectrode 11 (see also FIG. 9).

Figure 1D:
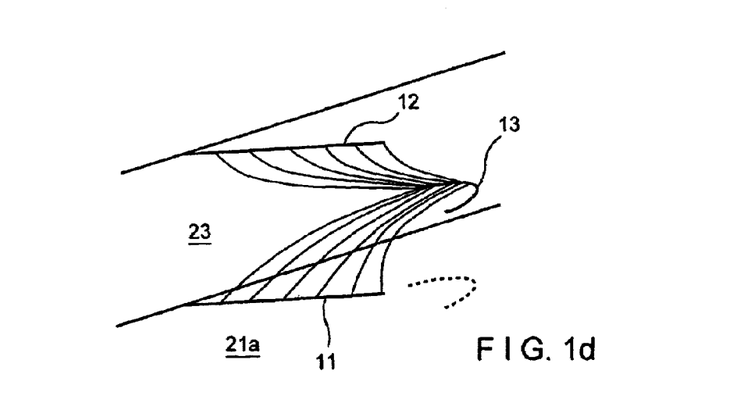

FIG. 1d shows the above-mentioned third variant with a three-dimensional electrode arrangement. The microelectrodes 11, 12 are on the bottom or cover surfaces of the channel while the auxiliary electrode 13 with a suitable confinement is arranged in the middle of the channel (see also FIG. 10). As a result of the auxiliary electrode 13, the field lines between the microelectrodes 11, 12 are distorted, resulting in the curved reference surface, shown hatched (shown in part only).

The illustrated reference surfaces only represent the positions of the field barriers without illustrating the forces acting in the respective regions, i.e. the height of the field barriers. Essentially the acting forces depend on the density of the field lines and the passive electrical characteristics of the particles to be manipulated in the respective channel region. The functional field barriers according to the invention are thus influenced by the geometric shape of the microelectrodes which combine their effect, both in relation to their shape (curvatures etc.) because the dielectrophoretic repulsion forces are essentially positioned perpendicular to the reference surfaces, and in relation to their areas (field line density).

Figure 2:
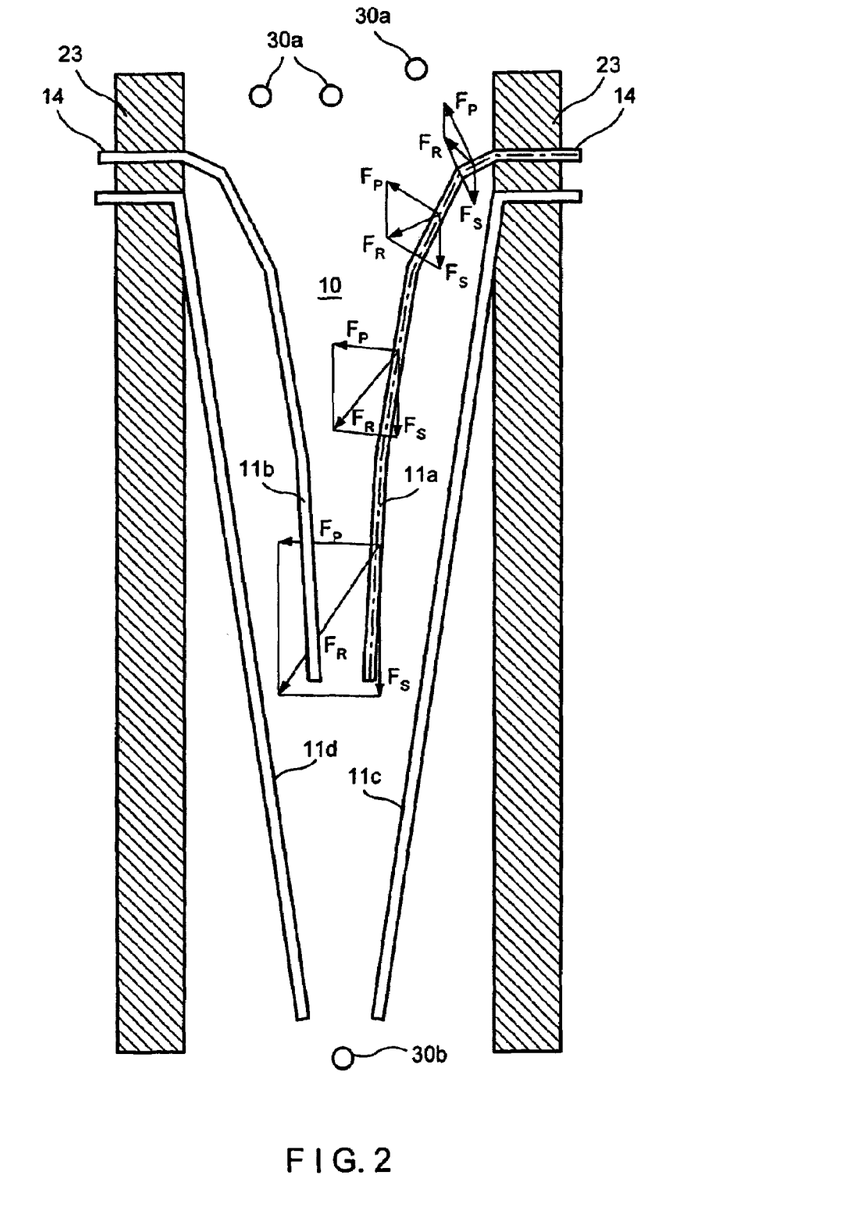
FIG. 2 illustrates a diagrammatic top view of band-shaped curved microelectrodes.

FIG. 2 shows an electrode arrangement 10 according to the invention according to the above-mentioned first variant. Microelectrodes 11a, 11b are arranged on the bottom surface 21a of the channel of a microsystem, said channel being laterally delimited by the spacers 23. High-frequency electrical potential is applied to the microelectrodes 11a, 11b via the control lines 14; said microelectrodes 11a, 11b act in combination to form a so-called particle funnel as follows.

The electrode arrangement 10 is intended to touchlessly focus, onto the middle line of the channel, the particles 30a flowing along the entire width of the channel or the entire volume, as is shown by the position of particle 30b. This arrangement has the advantage of optimising the electrode bands in relation to ensuring deflection (focussing) of the suspended particles, a shortening of the electrode arrangement in longitudinal direction of the channel and a reduction in electrical losses at the microelectrodes.

In this embodiment of the invention, the basic idea of the design of the microelectrodes consists of adapting the curvature of the reference surfaces formed by the field barrier, to the flow forces in the channel. For in microsystems with channel dimensions below 500 pm, due to the Reynolds number being low at these dimensions, laminar flows with predefined flow profiles form. The flow speed near the channel walls is lower than that in the middle of the channel (flow speed directly at the channel wall equals zero). As a result, the flow forces occurring near the channel walls are less than those in the middle of the channel. This makes it possible to manipulate the particles at the edge of the channel with lesser polarisation forces or with polarisation forces more steeply directed against the flow forces than in the middle of the channel. The combined effect of the flow forces and polarisation forces is explained below. If essentially the same polarisation forces are formed along the entire length of the microelectrodes, it is sufficient for safe deflection, for the particles to be manipulated, at the edge of the channel to encounter microelectrodes protruding more steeply into the channel than they do in the middle of the channel. This makes it possible to achieve a significant shortening of the microelectrodes (see below)

In FIG. 2 the forces acting on the particles are illustrated as an example in individual sections of the microelectrode 11a. The respective total force is composed from the electrically-induced repulsion force Fp (polarisation force) and the driving force Fs which is exerted by the flow of the suspension liquid or from the exterior (e.g. in centrifugal systems as centrifugal force). The resulting total force FR results from vector addition of forces Fp and Fs. If the vector of the total forces FR does not intersect the field barrier of the microelectrode 11a, then a particle is safely deflected. The force diagrams in FIG. 2 illustrate that the driving force Fs increases towards the middle of the channel. To meet the above-mentioned condition of safe particle deflection, accordingly the angle between the alignment of the microelectrode 11a and the longitudinal direction of the channel changes from a steeper angle at the edge of the channel to a shallow angle (near-parallelity) in the middle of the channel.

Thus the microelectrodes 11a, 11b are curved depending on the flow profile. In the embodiment shown, each of the band-shaped microelectrodes consists of a multitude of straight electrode sections. But in a variation of this embodiment, a steady curvature can be provided. Corresponding to the parabolic or hyperbolic flow profile occurring in laminar flows, the curvature is also parabolic or hyperbolic.

According to the invention, the microelectrodes 11a, 11b form the field barriers along a curved reference surface.

The microelectrodes 11c, 11d are not provided for in practical application; in the illustration they serve the purpose of comparing an arrangement according to the invention of polygonally curved microelectrodes with straight electrode bands providing the same deflection performance. It has been found that the microelectrodes 11a, 11b according to the invention are considerably shorter.

The narrow electrode bands shown in FIG. 2 are very sensitive to faults in workmanship and local interruptions. A hairline crack at the shoulder of a band-shaped microelectrode leads to failure of the entire microelectrode. This can be overcome by an electrode design as shown diagrammatically in FIG. 3. The structuring and covering technique described in relation to FIG. 3 can also be implemented with other embodiments of the invention.

Figure 3:
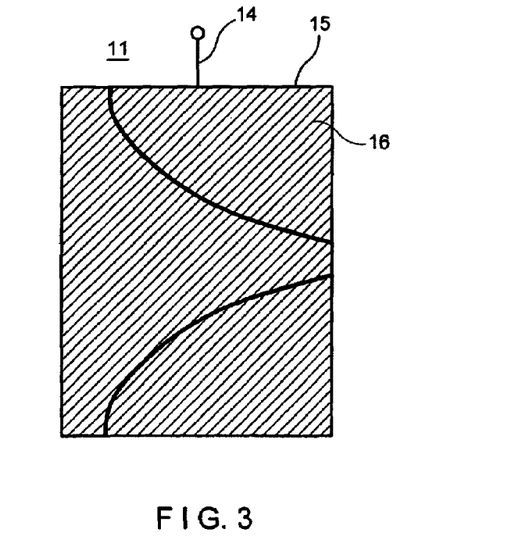
FIG. 3 illustrates a diagrammatic top view of a modified design of band-shaped curved microelectrodes.

FIG. 3 shows a microelectrode 11 with a control line 14. The electrode 11 consists of an electrically conductive layer 15 which carries an electrically non-conductive insulation layer or cover layer 16. The insulation layer 16 comprises structured recesses which expose the layer 15. In FIG. 3 the insulation layer 16 is shown hatched, while the (e.g. metallic) layer 15 is shown in black. Structuring of the insulation layer takes place according to the desired form of microelectrodes which in the example shown are arranged to form a particle funnel as shown in FIG. 2. The electrical field lines emanate from the metallic layer 15 into the channel only in the regions of the recesses, so that again field barriers with reference surfaces that are curved in an application-specific way are formed. This arrangement has the advantage that a small interruption of the exposed sections of the metallic layer 15 (i.e. of the microelectrode) does not lead to failure because the respective potential is also applied to the remaining metallic layer 15. For example the thickness of the layer 15 is approx. 50 nm to several pm, typically approx. 200 nm. The thickness of the insulation layer is around 100 nm to several pm. Preferably the insulation layer 16 comprises biocompatible materials (e.g. oxides, SiO2, SiNO3 and the like, polymers, tantalum compounds or the like).

Below, a further embodiment of the electrode arrangement 10 according to the above-mentioned first variant is explained with reference to FIGS. 4a to 4c. An important application of fluidic microsystems consists of sorting the suspended particles depending on their passive electrical characteristics (hereafter referred to as polarisation characteristics during negative dielectrophoresis). Polarisation characteristics depend on the dielectric properties of the particles and their dimensions. The dielectric characteristics of biological cells are a sensitive indicator of certain cell characteristics or cell changes which per se could not be detected for example by monitoring cell size.

Sorting of particles depending on their passive electrical characteristics is based on the following principle. Whether or not a particle can pass the field barrier formed by a sorting electrode depends on whether or not the resulting force from driving force Fs and polarising force Fp (see above) intersects the field barrier. If the resulting total force FR points through the field barrier, then the particle moves in this direction, i.e. the sorting electrode is passed. However if the resulting force FR points to a region located upstream in relation to the sorting electrode, then the particle will move in this direction and will not be able to pass the sorting electrode. As explained above, the resulting force FR depends on the flow speed in the channel and thus the x position of the particles. The flow speed increases towards the middle of the channel. Thus particles of relatively high polarisability which cannot pass the sorting electrode at the edge of the channel, are subjected to a stronger driving force Fs towards the middle of the channel, so that they may then possibly move past the sorting electrode. The change in flow speed in x-direction follows the flow profile; as a rule it is non-linear. Accordingly, the use of a straight sorting electrode would result in non-linear separation behaviour. The implementation of curved field barriers according to the invention compensates for this. To this effect, microelectrodes 41a, 41b with a curvature depending on the flow profile are used according to the principles explained with reference to FIG. 2.

Figure 4A:
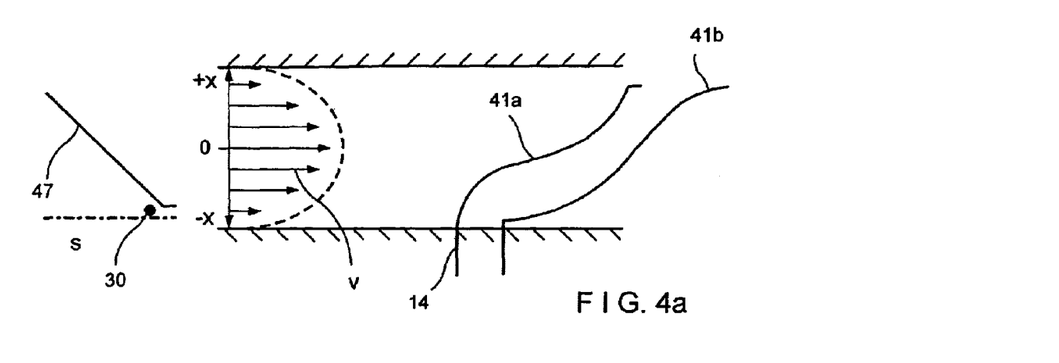
FIGS. 4a to 4c illustrates diagrammatic views for illustrating sorting electrodes for particle sorting.

FIG. 4a shows two examples of curved microelectrodes 41a, 41b on the bottom surface 21a of a channel between lateral spacers 23. The flow in the channel is in y direction from left to right, with the arrows v showing the speed-flow profile in the channel. Upstream, in front of the actual sorting electrode 41a or 41b there is a straight microelectrode 47 whose task is to focus to a start line s, the particles 30 flowing in from the left. The microelectrode 47 can also be designated a focussing electrode. It can be a straight conventional deflector electrode (as shown) or a curved deflector electrode. Downstream of the focussing electrode 47, one of the sorting electrodes 41a or 41b is arranged whose task consists of leading the inflowing particles 30 into different tracks in x-direction in the channel, depending on their polarisation characteristics. Particles with a high polarisability should move onward in different tracks in y-direction than particles with a low polarisability 30b.

The sorting electrode 41a is set up for linear force effect. For this purpose the curvature of the microelectrode is shaped according to the flow profile. If the flow speed is low, the setting angle between the microelectrode and the y-direction is steep; if the flow speed is high, the setting angle is more shallow. Thus the microelectrode 41a is S-shaped with a turning point in the middle of the channel. After a particle has passed the sorting electrode 41a there is a linear relationship between the x-co-ordinate of the particle and its polarisability. If a non-linear sorting effect is intended, then the microelectrode can be curved like the sorting electrode 11b. The curvature is less pronounced than is the case with sorting electrode 11a so that the influence of the driving force Fs is not compensated for by the flow speed. Depending on the relationships set, a non-linear influence arises between the x-position of the particles and their polarisability after passing the sorting electrode 11b. This configuration can in particular be used to separate two particle types of different polarisability.

Results of experiments show that with a sorting arrangement according to FIG. 4a, it was possible to neatly separate erythrocytes from so-called Jurkart cells, although both cell types were of the same size.

Figure 4B:
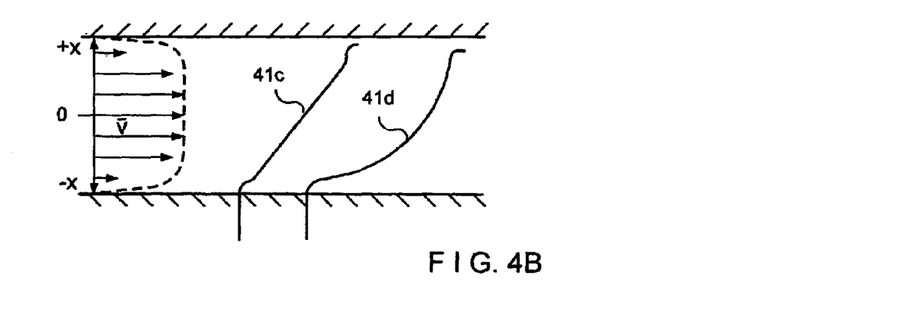

If the flow profile in the channel is not distinctly parabolic in shape as shown in FIG. 4a, but instead is plateau shaped, then sorting electrodes 41c, 41d according to FIG. 4b are provided. The flow speed first increases from the direction of the edge of the channel before remaining essentially constant in the middle section of the channel. So as to achieve a linear sorting effect, the band shape of sorting electrode 41a is straight, while at its ends there are curvatures to take into account the changing driving force Fs. For a non-linear sorting effect, the sorting electrode 41*d* is curved. From the shoulder of the sorting electrode 41*d* at the control connection 14 to its end there is an increasing effect of the field barrier.

Figure 4C:
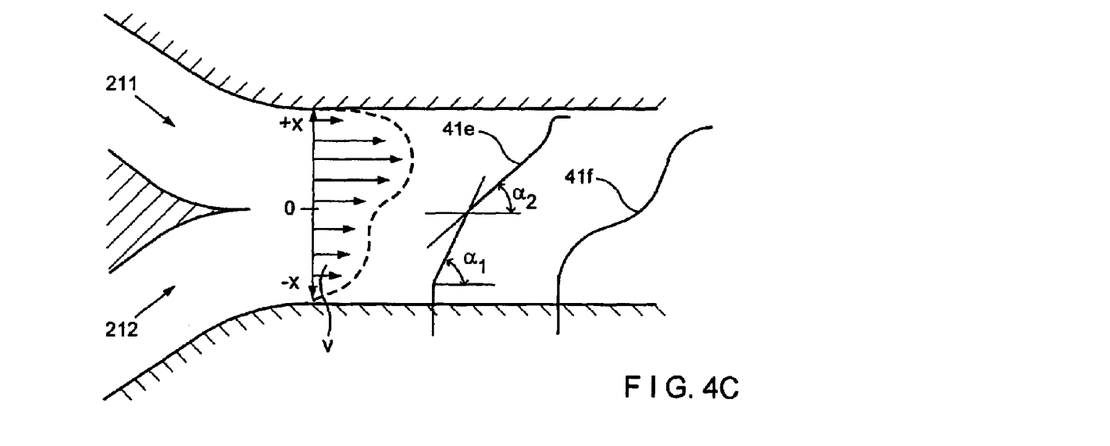

The shape of the sorting electrodes can also be adapted to more complicated flow profiles as is shown in FIG. 4*c*. In the microsystem 20 a first channel 211 with a high flow speed and a second channel 212 with a lesser flow speed join to form a joint channel 21. Due to the laminarity of the flow, the flow profile at first remains intact also in the common flow path. Accordingly, the sorting electrodes 41*e* or 41*f* are curved so as to achieve a particular linear or non-linear sorting effect. The lower the flow speed, the higher the setting angle between the direction of the microelectrode (alignment of the reference surface) and the longitudinal direction of the channel (y-direction).

For reasons of clarity, the focussing electrode 47 according to FIG. 4*a*, is not shown in FIGS. 4*b* and 4*c*.

The above-mentioned sorting takes place with the assumption that the potential is constant along the entire length of the microelectrode. In reality however, small electrical losses occur along the microelectrode so that the field barrier becomes progressively smaller from the shoulder of the microelectrode (at the control line) towards its end. This phenomenon can be taken into account in the curvature of the sorting electrodes in that at the side of the control line of the channel, a larger electrode curvature is provided than at the end of the sorting electrodes. But the phenomenon mentioned can also be purposefully used for additional non-linear separation effects. By using modified embodiments, the loss of potential towards the end of the microelectrodes can be amplified especially as a result of measures for forming field gradients. This means that the height of the field barrier formed by the microelectrode increases or decreases along the curved electrode band. Such gradient electrodes can be designed in a shape according to FIG. 5.

For particle sorting in relation to various groups of characteristics, several sorting electrodes according to FIG. 4 can be arranged in sequence in the direction of the channel. A characteristic potential or potential gradient at a predetermined frequency is applied to each sorting electrode. For example relatively low frequencies (in the region of approx. 10 kHz) can be used for sorting in relation to various dielectric membrane characteristics, and high frequencies (above 100 kHz) can be used for sorting depending on the cytoplasmatic conductivity of biological cells.

Figure 5:
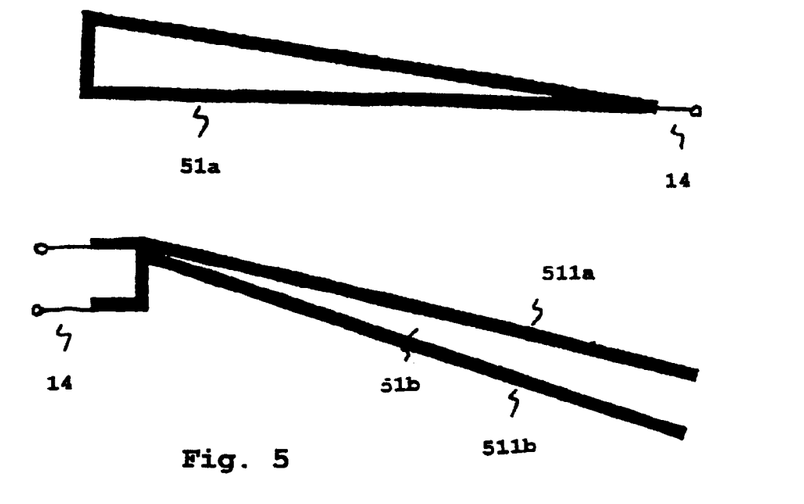
FIGS. 5a to 5b illustrates diagrammatic views of microelectrodes for generating field gradients.

FIG. 5 shows gradient electrodes 51*a*, 51*b*; for the sake of clarity, the electrode bands are straight. To set field barriers according to the invention, with curved surfaces, the gradient electrodes shown additionally comprise a characteristic application-specific curvature according to the principles explained above.

The gradient electrode 51*a* is formed by a closed electrode band around a triangular surface. As the distance from the control line 14 increases, the field line density is reduced in line with the fanning out of the triangle. The same applies to the gradient electrode 51*b* with two diverging partial bands 511*b* and 512*b*.

The collection and at least temporary arrangement of particles or particle groups in the channel through which suspension liquid flows, is a further important application of fluidic microsystems. To this effect, electrode arrangements according to the invention are shaped as collecting electrodes as is explained below with reference to FIGS. 6 to 8.

Figure 6A:
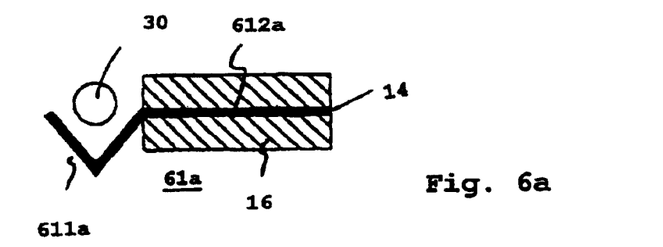
FIGS. 6a to 6e illustrates diagrammatic views of band-shaped collecting electrodes according to the invention.
Figure 6B:
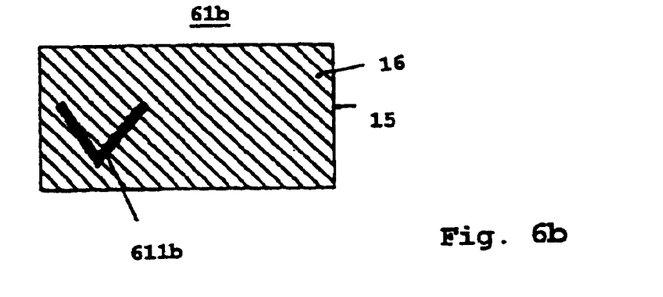

FIG. 6*a* shows the basic shape of a collecting electrode. Again, only one microelectrode on the bottom or cover surface of a channel is shown, which acts in combination with that of a second microelectrode located at the opposite side of the channel. A collecting electrode 61*a* comprises an electrode band with an angle section 611*a* and a supply section 612*a*. The angle section 611*a* forms an angle pointing in the direction of flow (x-direction). The opening angle of the angle section 611*a* is selected depending on the shape of the particles to be collected; preferably the opening angle is less than 90°, e.g. ranging from 20 to 60°. The opposing angle sections of electrodes whose effect is combined, form a barrier which the particles 30 to be collected cannot pass despite the driving force of the flow. This barrier is maintained as long as the collecting electrodes remain selected. The supply section 612*a* is electrically ineffective as a result of an insulation layer 16. FIG. 6*b* shows a modified embodiment of a collecting electrode 61*b* which is made with reference to the cover technique explained above with reference to FIG. 3. The electrically effective angle section 611*b* is formed by a recess in the insulation layer 16 as a result of which a deeper metallic layer 15 is exposed towards the suspension liquid containing the particles.

Figure 6C:
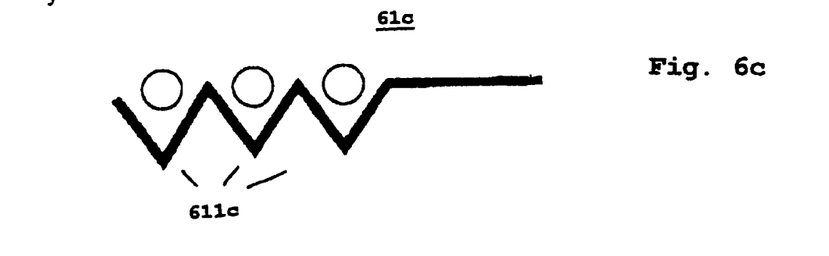
Figure 6D:
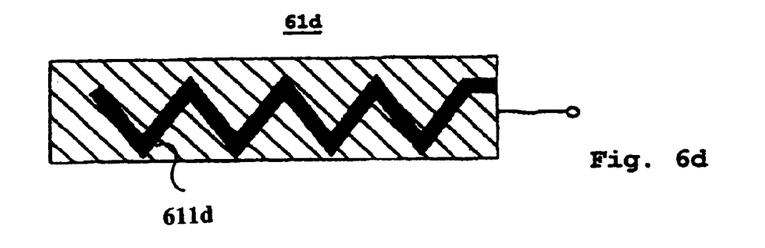

FIGS. 6*c* and 6*d* show corresponding collecting electrodes 61*c* and 61*d*, each comprising a multitude of angle sections 611*c* or 611*d*. These angle sections are again set to collect inflowing particles 30. By adjoining the angle sections 611*c* or 611*d* across the longitudinal direction (x-direction) of the channel, the particles flowing in the various channel sections can be collected selectively. A collecting electrode 61*c* or 61*d* is advantageously combined with one of the sorting electrodes according to FIGS. 4*a* to 4*c*. The sorted particles are separately collected in the individual collection regions of the collection electrodes. The collection electrode 61*d* essentially corresponds to the collection electrode 61*c*. This completes implementation of the entire cover technique.

The collection electrodes 61*c* or 61*d* are particularly well suited to line up particles in the suspension flow in the manner of a start line from which the particles flow onward simultaneously when the control potential of the collection electrodes is switched off.

Figure 6E:
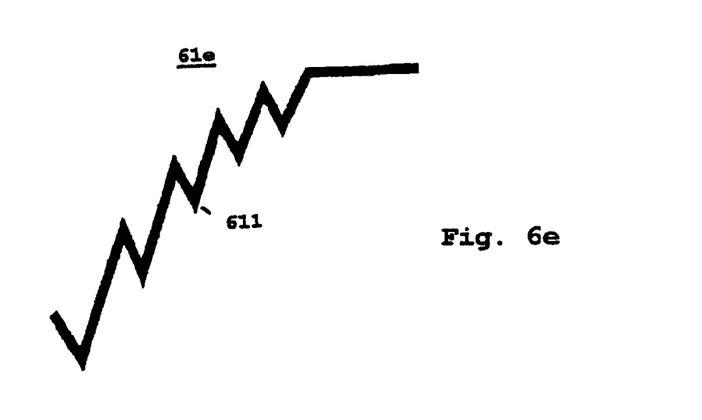

FIG. 6*e* shows a further embodiment of a collection electrode 61*e* where a multitude of angle sections 611*e* is also provided, but with the angle sections being designed for collecting or gathering particles of various sizes or various sized accumulations of such particles.

Figure 7A:
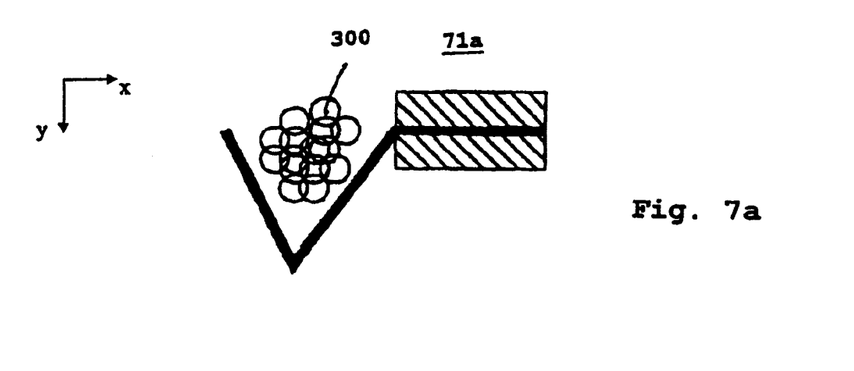
FIGS. 7a to 7c illustrates further embodiments of collecting electrodes according to the invention.

FIG. 7*a* shows the accumulation of a particle group 300 using a collecting electrode 71*a*. This embodiment of a collecting electrode differs from the collecting electrode according to FIG. 6*a* only in its dimensions. This design is particularly well suited to the formation of particle aggregates. Again, preferably a combination with a sorting arrangement according to FIGS. 4*a* to 4*c* is implemented.

Figure 7B:
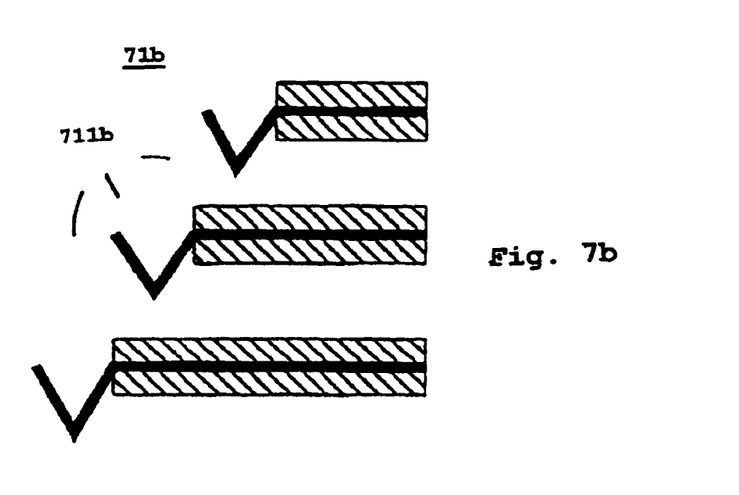

The electrode arrangement according to FIG. 7*b* is configured for separate collection of particles or particle groups from the suspension flow in the channel which differ in relation to their flow track in x-direction. The microelectrode arrangement 71*b* comprises several partial collection electrodes each with an angle section 711*b*, whereby each partial collection electrode can be selected separately. When combining such a collecting electrode arrangement with a sorting arrangement according to FIGS. 4*a* to 4*c*, the following method can be implemented with particular advantage.

First a particle mixture which flows through the channel in the microsystem is sorted depending on the passive electrical characteristics of the particles, and in this way is guided to various tracks mutually spaced apart in x-direction. Then in a collection electrode according to FIG. 7b, particle-type specific collection of the particles flowing in the individual tracks takes place. By releasing the partial collection electrodes according to a time sequence (in each instance by switching off the control potential), the previously sorted particles can flow on in groups in the microsystem. Downstream, the channel can for example be split into several sub-channels, with the groups of particle types specifically being directed to said sub-channels.

Figure 7C:
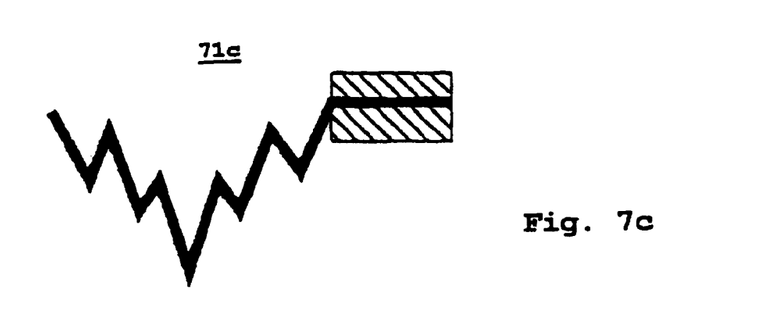

FIG. 7c shows a further collecting electrode 71c for generating a predetermined particle formation.

Depending on the application, the angle sections of the collecting electrodes shown in FIGS. 6 and 7 can extend across the entire width of the channel or only across parts of the channel. Within an electrode arrangement, collecting electrodes can be provided for individual particles and/or for particle groups.

Figure 8:
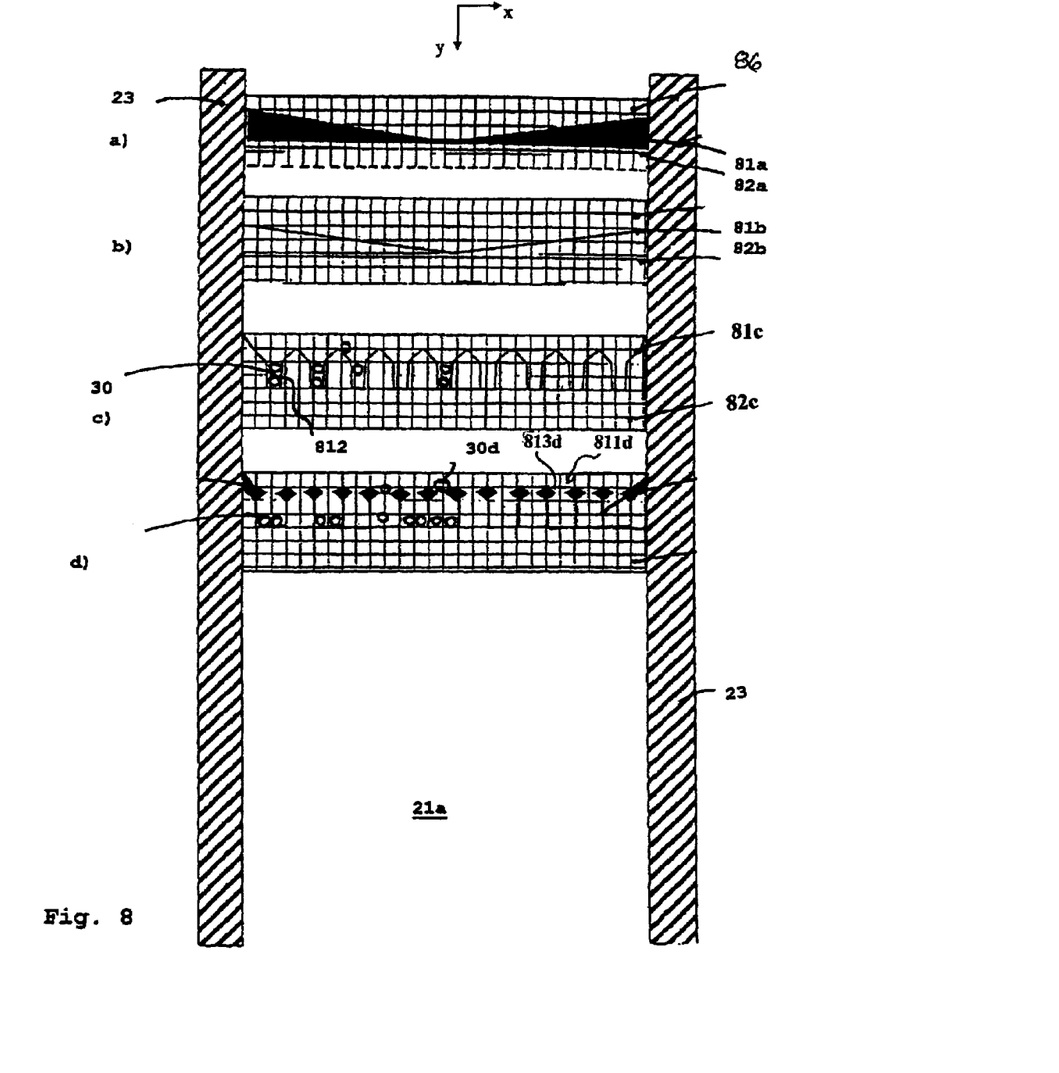
FIG. 8 illustrates a top view of various electrode arrangements for generating curved field barriers.

Further embodiments of combined sorting electrodes and collection electrodes are shown in FIG. 8 in top view of the bottom surface 21a of a channel delimited by spacers 23. The suspension liquid with suspended particles flows through the channel in y-direction. According to FIG. 8a an area-shaped microelectrode 81a on the bottom surface 21a and a straight band-shaped microelectrode 82a (shown by a dashed line) on the opposite surface of the channel, act in combination. The planar-shaped microelectrode 81a has been produced using the cover technique explained above. A metallic layer supports an insulation layer with a recess according to the shape of the microelectrode 81a (drawn in black). The field lines between the microelectrodes 81a and 82a are inhomogenously aligned across the direction of flow, resulting in an asymmetric field barrier or again a reference surface which is curved according to the invention. In the middle of the channel the field line density is largest so that the electrically generated forces are located in the region of the highest flow speed. In this way an essentially constant balance between the driving force resulting from the flow and the electrical polarisation force is formed in x-direction across the width of the channel. According to FIG. 8b, again a field barrier with a curved reference surface is formed. The microelectrodes 81b, 82b are both designed so as to be linear or band-shaped, they are not arranged in opposite positions but instead offset in relation to each other.

FIG. 8c shows an electrode arrangement for forming particle aggregates. The microelectrodes 81c, 82c form a number of funnel-shaped particle collectors arranged side by side. Each particle collector 81 is formed by a field barrier which in the direction of the flow of liquid first narrows in the form of a funnel before discharging into a straight channel section 812. The channel section is dimensioned such that two particles can be arranged one behind the other in the direction of flow. Due to the formation of adhesion forces, the particles form an aggregate (so called pair-loading in the direction of flow). The embodiment according to FIG. 8d is a modified version in that pair-loading takes place across the direction of flow. The individual collector elements 811d comprise electrode tips 813d on the inlet side. With these electrode tips 813d an additional barrier effect or filter effect can be achieved, and already existing aggregates or larger particles 30d can be precluded from assembling in the collecting electrode 81d.

Figure 9:
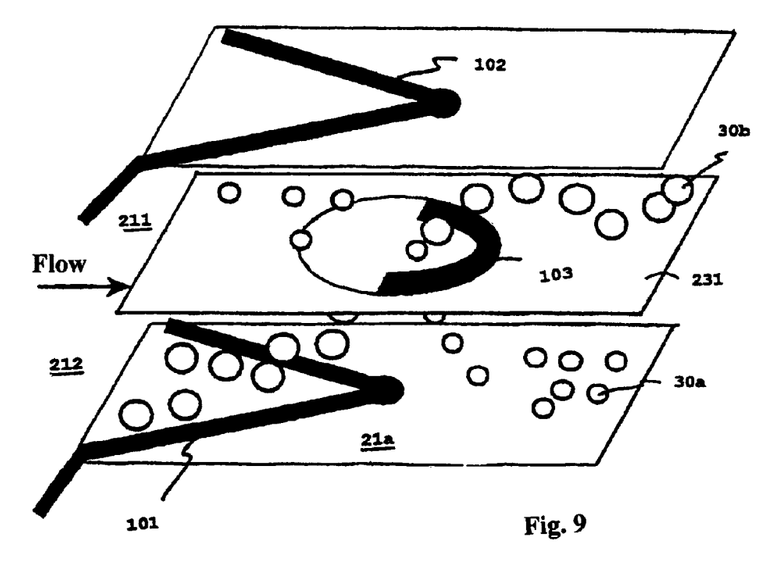
FIG. 9 is corresponding to FIG. 1d.

FIG. 9 (corresponding to FIG. 1d) shows an embodiment of an electrode arrangement according to the above-mentioned third variant. In a microsystem, again two sub-channels 211, 212 extend parallel to each other and separated from each other by a separation wall 231 comprising an aperture 232. The electrode arrangement according to the invention comprises microelectrodes on the bottom surfaces and cover surfaces in the form of focussing electrodes 101, 102 and the auxiliary electrode 103. The auxiliary electrode is arranged at the separation wall 231, adjacent to the aperture 232, on the downstream side of the aperture 232. The auxiliary electrode 103 does not comprise a control line. It merely serves to form the reference surface of the field barriers formed by the electrode arrangement. The effect of the microelectrodes is combined as follows.

Focussing electrodes 101 and 102 are used to focus the particles 30a, 30b, flowing in the sub-channels 211 or 212, to a middle line according to the position of the aperture 232 in the separation wall 231. The particles are deflected by the field barrier between he focussing electrode 101 and the auxiliary electrode 103 or between the focussing electrode 102 and the auxiliary electrode 103, through the aperture 232, into the adjacent sub-channel or they are left in the respective sub-channel. According to a preferred method, the focussing electrodes 101, 102 are operated at various frequencies so as to act in a particle-selective manner. Accordingly, again selective particle sorting into the sub-channels, or deflection of predetermined particles to an adjacent sub-channel can be achieved to carry out a particular treatment of the active ingredient with the respective suspension liquid provided in said sub-channel.

Figure 10:
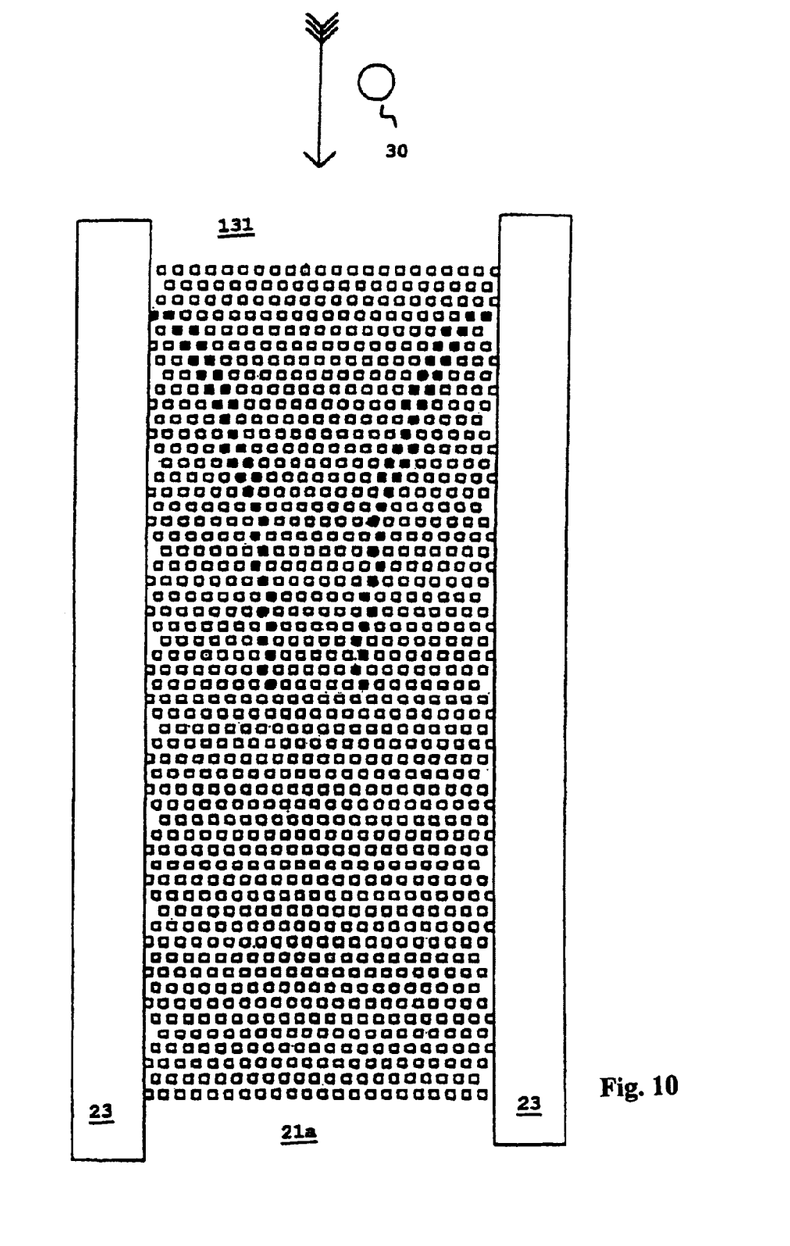
FIG. 10 illustrates a diagrammatic top view of a segmented electrode arrangement.

According to a particular aspect of the invention, the microelectrodes in the individual embodiments can be segmented per see However, in this case each microelectrode comprises a number of electrode segments which are arranged according to the desired electrode function. FIG. 10 shows a particularly versatile microelectrode 131 as an array of a multitude of pixel-shaped electrode segments arranged matrix-like. The electrode segments are arranged across the entire width of the bottom surface 21a between the spacers 23 and can be selected individually. This makes it possible to form the desired curved field barriers in particular according to the above-mentioned first variant, depending on the concrete application, in particular depending on the particles to be manipulated, the flow conditions and the task of the microsystem. In FIG. 13 the presently selected pixels are shown in black while the pixels which are not selected are shown in white. In this case the segmented microelectrode 131 assumes the function of a particle funnel according to FIG. 2 by means of which the particles 30 are focussed to the middle of the channel.

The pixel-shaped electrode segments make possible loss-minimising focussing, sorting or collecting of particles. Each electrode segment can be selected with its own potential value (voltage) or its own frequency. In this way any specified dielectric force field can be generated along the channel. For example the influence of the flow profile can be compensated for in that the pixels arranged across the longitudinal direction of the channel are selected with a voltage which corresponds to the square root of the profile of the flow speed.

The size of the electrode segments and spacings between the electrode segments are preferably smaller than the characteristic dimension of the particles to be manipulated, but they can also be larger.

All particle manipulation takes place contact-free, so that the microsystems according to the invention are particularly suitable for manipulating biological cells or cell components.

The microsystems are further characterised in that they may comprise apertures (inflows, through-flows, outflows) which can be closed off so that after or before centrifugation, the particles can easily be removed or inserted. Furthermore, all the microelectrode elements (holding electrodes for particles, microfield cages etc.) can be installed which are known per se for dielectrophoretic influencing of particles, and which are used in conventional microsystems which operate with flowing liquids. Based on the combined action of gravitational or centrifugal forces with dielectrophoretic forces, the method according to the invention is an electrically controlled or active centrifugation. Furthermore, combinations can be provided with the effect of optical forces (laser tweezers), magnetic forces (influence on magnetic particles), or mechanical forces in the form of ultrasonic forces.

Areas of application of the invention include in particular: cell separation/cell fractionation, cell sorting, cell loading (molecular, nano-particles, beads), cell discharge (molecular), cell permeation (so-called electroporation), cell fusion (so-called electrofusion), cell pair formation, and cell aggregate formation.

The invention is not limited to particular solution liquids or suspension liquids. It is advantageous if the viscosity of the liquid contained in the microsystem is known. If the viscosity is known, the rotational speed for setting a particular particle speed can be determined on the basis of tabular values or by means of a program algorithm. Alternatively, it is however also possible to acquire the actual speed of the particles in the microsystem during centrifugation (e.g. by using an optical sensor) and to regulate the rotational speed for setting a particular particle speed. It can be provided that in various sub-sections of the channel structures, e.g. in parallel channels which are interconnected only via an aperture, liquids of various viscosity are contained. In this case however, viscosities are preferred which ensure that diffusion of the liquids through the aperture is relatively low or negligible over the entire period of centrifugation.

If the mass density of the particles is less than that of the liquid in the microsystem, the invention can be implemented with corresponding modifications in that particles are introduced on the side of the microsystem away from the axis of rotation. They then move to the other end of the microsystem under the influence of buoyancy or by the combined effect of buoyancy and centrifugal forces.

The microsystem is designed corresponding to the channel structure and alignment of the electrodes in dependence on the particular application. As a rule, the cross-sectional dimensions of channels are significantly larger than the diameter of individual particles. Advantageously, this prevents blocking of the channels. If only particles with particularly small dimensions have to be manipulated (e.g. bacteria or viruses or cell organelles), then the channel dimensions can be reduced accordingly, e.g. to dimensions below 10 pm.

The invention is implemented with a microsystem which is closed off at least on one side. The closed end can be a closed-off end of a channel, a closed-off collection zone or a closed-off hollow space in the microsystem. With particle manipulation according to the invention, there is essentially no movement of liquid towards the closed end. In particular with implementation of collection zones or hollow spaces at the closed-off end, this means that these, like the entire microsystem, are filled with the solution or suspension for the particles at the beginning of particle manipulation.

If during manipulation of the particles, agglomerations or temporary blockages of the channel structures occur, according to the invention it is provided to temporarily increase the rotational speed of the centrifuge so as to detach the adhering particles and move them on.

The invention claimed is:

1. A microsystem adapted for dielectrophoretic manipulation of particles in a suspension liquid, said microsystem comprising:
    a channel with walls, said channel having a longitudinal extension in an x-direction and said channel walls comprising bottom and cover surface walls extending in the x-direction and an y-direction, and
    an electrode arrangement on at least one of said bottom or cover surface walls for generating a field barrier which crosses the channel at least partly, wherein
    said electrode arrangement comprises at least one microelectrode having a band-shape, and
    in relation to the longitudinal extension of said channel, said band-shape has a predetermined parabolic or hyperbolic curvature along its length so that the field barrier has a corresponding parabolic or hyperbolic curvature.

2. The microsystem according to claim 1, in which the electrode arrangement comprises at least two microelectrodes of the same shape and alignment affixed on opposite channel walls, each of said at least two microelectrodes being in the shape of a curved band.

3. The microsystem according to claim 2, in which the at least two microelectrodes depending on a flow profile of said suspension liquid flowing though said channel are curved such that in every section of a field barrier of the microelectrodes a resulting force acting on a particle in said suspension liquid points to a region which is situated upstream in relation to the microelectrode.

4. The microsystem according to claim 3, in which the at least two microelectrodes comprise four microelectrodes being arranged as focusing electrodes to form a particle funnel.

5. The microsystem according to claim 2, in which the at least two microelectrodes adapted to a flow profile of said suspension liquid flowing through said channel are curved such that a resulting force acting on a particle from one end of each of the microelectrodes towards the other end describes a change in direction which leads from a region situated upstream to a region situated downstream respectively in relation to the at least two microelectrodes.

6. The microsystem according to claim 5, in which the at least two microelectrodes are sorting electrodes providing a field barrier in combination with the flow profile of the suspension liquid in the channel such that each of the suspended particles with different passive electrical characteristics can pass the sorting electrodes on a separate track depending on the characteristics of said suspended particles.

7. A microsystem adapted for dielectrophoretic manipulation of particles in a suspension liquid, said microsystem comprising:
    a channel with channel walls, said channel having a longitudinal extension in an x-direction and said channel walls comprising bottom and cover surfaces walls extending in the x-direction and an y-direction, and
    an electrode arrangement with at least one microelectrode on at least one of said bottom or cover surfaces walls for generating a field barrier which crosses the channel at least partly, wherein
    the at least one microelectrode comprises a multitude of straight electrode sections connected with each other, and—in relation to the longitudinal extension of said channel, said straight electrode sections are arranged with predetermined, different angles and the field barrier has a parabolic or hyperbolic curvature relative to the x- and y-directions corresponding to the arrangement of said straight electrode sections.

8. The microsystem according to claim 1 or 7, wherein at least two microelectrodes of the electrode arrangement are arranged in pairs on the bottom and cover walls of the channel.

9. The microsystem according to claim 1 or 7, in which at least one microelectrode of the electrode arrangement comprises two microelectrodes being provided on two opposite channel walls, comprising different geometric shapes.

10. Method of dielectrophoretic manipulation of particles in a suspension liquid, using a microsystem according to claim 1 or 7, said method comprising the steps of:

flowing said suspension liquid through the channel of said microsystem, forming a field barrier with a predetermined curvature relative to the direction of flow of said suspension liquid, and deflecting, sorting, collecting and/or forming microscopic particles under the influence of said field barrier.

\* \* \* \* \*